United States Patent
Shukla et al.

(10) Patent No.: US 6,466,813 B1
(45) Date of Patent: Oct. 15, 2002

(54) METHOD AND APPARATUS FOR MR-BASED VOLUMETRIC FRAMELESS 3-D INTERACTIVE LOCALIZATION, VIRTUAL SIMULATION, AND DOSIMETRIC RADIATION THERAPY PLANNING

(75) Inventors: Himanshu P. Shukla, Gates Mills, OH (US); Krishna K. Gadepalli, San Jose, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/620,319

(22) Filed: Jul. 22, 2000

(51) Int. Cl.$^7$ .................................................. A61B 5/05
(52) U.S. Cl. ............................. 600/411; 600/1; 600/2; 600/410; 600/414; 600/425; 600/426; 600/427; 382/128
(58) Field of Search .................................. 600/407, 411, 600/410, 414, 416, 2, 425, 426, 427; 382/128, 1

(56) References Cited

U.S. PATENT DOCUMENTS

| | | | | |
|---|---|---|---|---|
| 4,977,505 | A | * 12/1990 | Polizzari et al. | 364/413.19 |
| 5,211,164 | A | * 5/1993 | Allen | 128/653.1 |
| 5,706,810 | A | * 1/1998 | Rubinsky et al. | 128/653.1 |
| 5,734,692 | A | 3/1998 | Seki | |
| 5,859,891 | A | 1/1999 | Hibbard | |
| 6,175,655 | B1 | * 1/2001 | George, III et al. | 382/257 |
| 6,175,761 | B1 | * 1/2001 | Frandsen et al. | 600/436 |
| 6,249,594 | B1 | * 6/2001 | Hibbard | 382/128 |

FOREIGN PATENT DOCUMENTS

WO  PCT WO 99/31289  7/1999

OTHER PUBLICATIONS

XP–001051542—Radiosurgical Treatment Planning of Brain Metastases Based on a Fast, Three–Dimensional MR Imaging Technique—by Lothar R. Schad, et al., 1993.
XP–00105146—The use of a Permanent Magnetic Resonance Imaging System for Radiotherapy Treatment Planning of Bone Metastases—by Takashi Mizowaki, et al., 2000.
International Search Report—International Application No. PCT/US 01 /22654—Jul. 18, 2001.

* cited by examiner

Primary Examiner—Marvin M. Lateef
Assistant Examiner—Jeoyuh Lin
(74) Attorney, Agent, or Firm—Fay, Sharpe, Fagan, Minnich & McKee, LLP (57) ABSTRACT

A method and apparatus are provided for MR based volumetric frameless 3-D interactive localization, virtual simulation, and dosimetric radiation therapy planning. Using an MR imaging device, a patient is scanned to generate a magnetic resonance image volume data set. Using the MR data set exclusively, parallel and divergent volume images of the patient is displayed for target tissue identification, localization, virtual simulation, and dosimetric radiation therapy planning. Preferably, the interactive localization, simulation, and dosimetric RTP is based exclusively on the 3-dimensional MR volume data set rendered in the form of at least one of a multi-planar reformatted image (MPR), an oblique multi-planar reformatted image (OMPR), a digitally reconstructed "radiograph" (DRR), and a digitally composited "radiograph" (DCR).

36 Claims, 5 Drawing Sheets

METHOD AND APPARATUS FOR MR-BASED VOLUMETRIC FRAMELESS 3-D INTERACTIVE LOCALIZATION, VIRTUAL SIMULATION, AND DOSIMETRIC RADIATION THERAPY PLANNING

BACKGROUND OF THE INVENTION

The present invention relates to the art of radiation therapy planning and, more particularly, to a method and apparatus for performing soft tissue tumor localization, virtual simulation, and dosimetric planning using volumetric frameless 3-dimensional magnetic resonance (MR) imaging data exclusively.

MR imaging data is used as the primary data set. Data acquired by other modalities such as CT, nuclear medicine, ultrasound, and others can be used as a secondary data set in conjunction with the primary MR imaging data. In that case, the secondary data is used for visualization assistance and the primary MR data is used for localization, virtual simulation and dosimetric planning.

In the past, computed tomography (CT) imaging has been used in connection with radiation therapy planning. The CT imaging data is the only data set used. In prior CT simulation systems, however, soft tissue tumors cannot be clearly identified in the acquired image. Accordingly, for those cancers, oncologists and radiation therapy planning (RTP) specialists must guess at the target location and size of the tumor based on experience. Bony structures provide only reference landmarks within the image. Therefore, the usual practice during planning is to "overstate" the area within the patient for subsequent dosimetric treatment. In that way, the radiation beam is sure to hit the intended target. However, one disadvantage to the above is that otherwise healthy tissue is also thereby unnecessarily irradiated.

An improvement over the CT simulation systems is provided by the so-called "CT with registered MR" process or simply "registration process." That process uses the CT imaging data as the primary data set for localization, virtual simulation, and dosimetric planning. The MR imaging data set is used as a secondary data set for visualization assistance.

Figure 1:
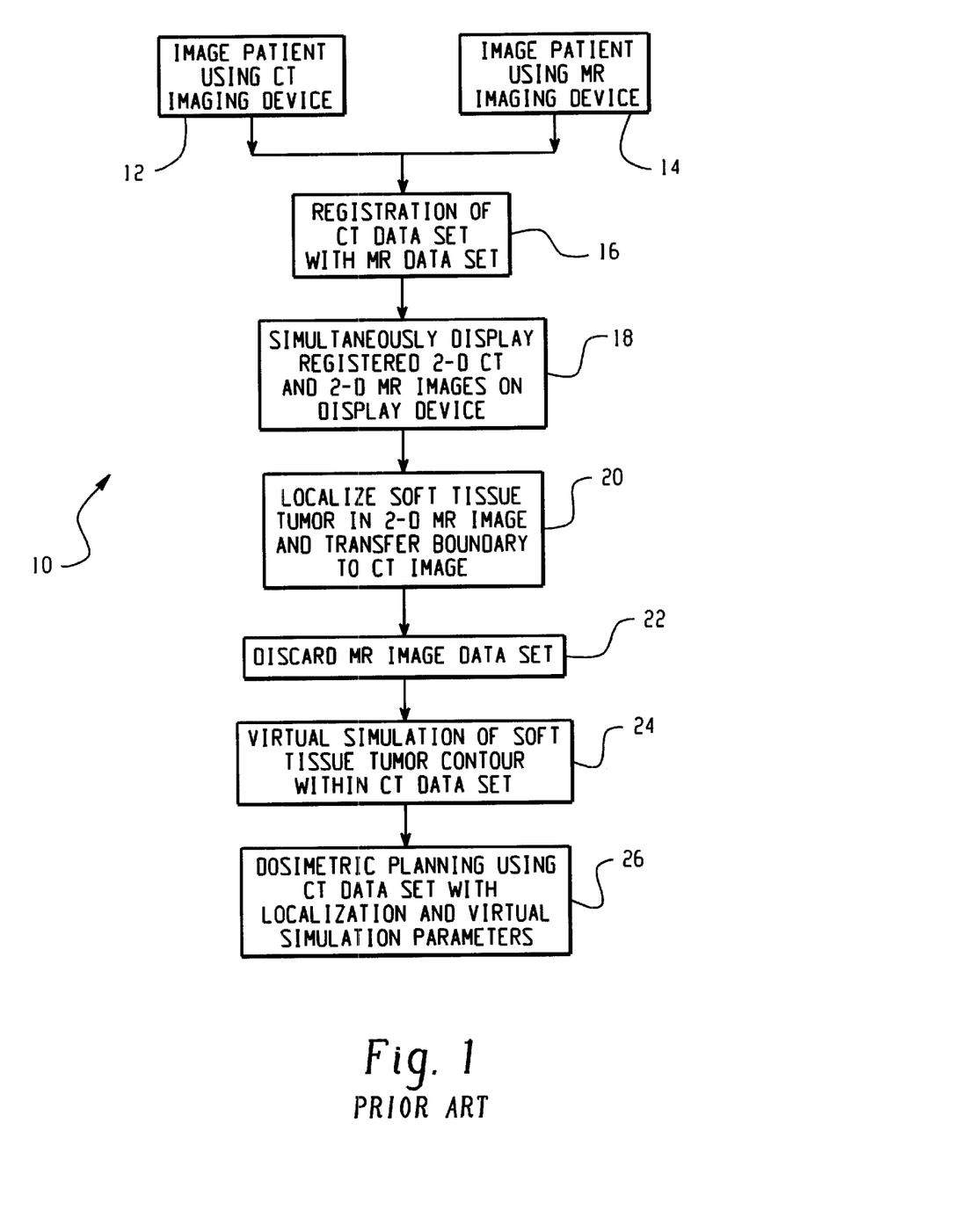
FIG. 1 is a prior art CT and MR image registration process for radiation therapy planning.
Figure 2:
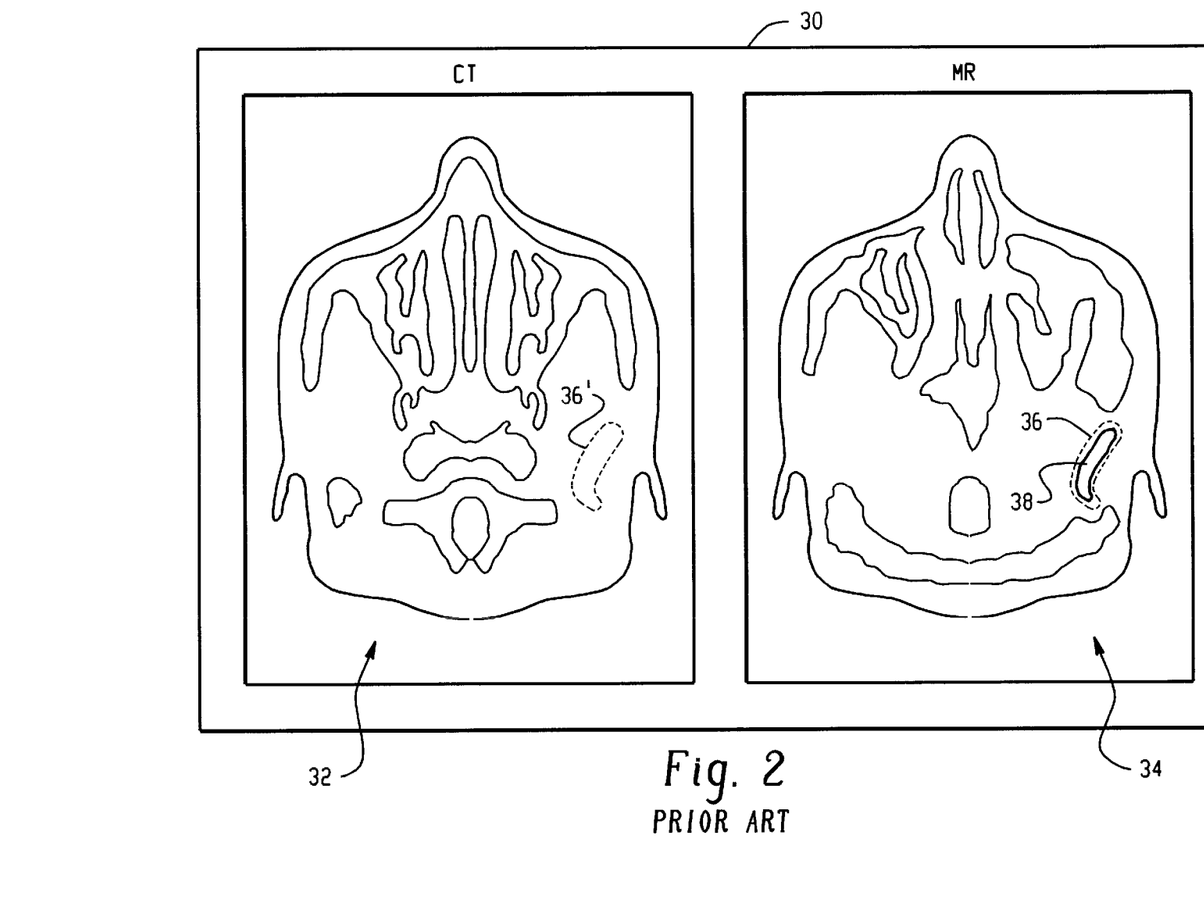
FIG. 2 is an illustration showing the simultaneous display of a CT image registered with an MR image according to the prior art method of FIG. 1.

A simplified form of registration process currently performed in connection with radiation therapy planning is shown in FIGS. 1 and 2. With reference now to those figures, the CT/MR registration process 10 usually begins with a pair of patient imaging steps. A CT imaging step 12 is performed on the patient using a suitable CT imaging apparatus. An MR imaging step 14 is also performed on the patient using a suitable MR imaging device, typically located in the hospital radiology department. One disadvantage to the CT with registered MR process is that oftentimes, the CT imaging apparatus is spaced a considerable distance from the MR imaging system. The need to move the patient from one site to another takes time and causes equipment and staff scheduling difficulties. The CT imaging device capital and usage costs add additional expense to patient treatment planning.

At step 16, the CT data set is registered with the acquired MR data set so that substantially identical CT and MR slice views of the patient can be displayed as a composite overlaid image or on respective CT and MR display devices 32 and 34 such as shown in FIG. 2. Preferably, to aid in visualization, the CT and MR displays 32, 34 are presented in a side-by-side relationship such as on an integrated display unit 30. The prior art registration process 10 includes means for simultaneously displaying the registered CT and MR images on adjacent screens or on a single screen in an image overlay at step 18.

Next in the current registration process, the soft tissue tumor is localized in the CT image by use of the MR image at step 20. The tissue localization step uses the CT data set as the primary data set and the MR data as the secondary data set. Localization in the 2-D CT images is greatly enhanced when the 2-D MR slice is displayed together with the 2-D CT slice on a single display monitor in an overlaid fashion. In prior art systems that use a side-by-side image display methodology such as shown in the drawing figure, the operator relies on soft tissue visualization in the MR image for localization in the primary (CT) data set. Typically, as shown in FIG. 2, this localization step includes a selection/definition and visual display of a target boundary 36 that can be adjusted in size, shape, and position manually by an operator using suitable operator interface controls such as a mouse, or the like. As further shown in FIG. 2, the target boundary 36 is traced over the outer edges of a soft tissue tumor 38 shown clearly in the MR display 34. As part of the registration step 16 and the simultaneous display step 18, a CT target boundary 36' is established in the CT display 32. The manual/operator movement of the MR target boundary 36 as well as changes in size and shape of the MR target boundary are "shadowed" by the CT target boundary display 36'. In that way, localization of the anatomical soft tissue tumor 38 in the MR display 34 causes a corresponding localization or "segmentation" of the CT target boundary 36' in the CT display 32 even though the soft tissue tumor 38 is not visible in the CT display 32. The MR image data set is discarded at step 22.

Next, in step 24, virtual simulation of the target boundary 36' is performed in the CT display 32. The treatment boundaries and beam modifiers are derived during virtual simulation using the tumor boundaries 36' in the CT display 32.

Dosimetric planning is executed in step 26 using the CT data set with the visualization and localization parameters derived from the CT image data.

One major disadvantage with the prior art CT with registered MR process for radiation therapy planning is the wasted time and expense attributable to the need for obtaining CT image data. As noted above, essentially, the MR image data is discarded early in the process.

To further exacerbate the problem, as shown in FIG. 2, soft tissue tumors cannot be clearly identified in the acquired CT image. Although an improvement over prior systems where CT image data forms the only data set, the CT with registered MR process continues to use the CT acquired image and display as the cornerstone of radiation therapy planning. The CT data set is used as the primary data set. As shown in FIG. 2, however, the essential data for localization and virtual simulation of soft tissue tumors is contained in the MR acquired image and display.

Lastly, as noted above, movement of the patient between the CT imaging device and the MR imaging device often causes problems in the registration step 16.

There is a need, therefore, for a method and apparatus for enabling soft tumor tissue localization, virtual simulation, and subsequent dosimetric planning using the MR acquired image exclusively. An improvement over the CT with registered MR process would be to skip the steps of acquiring the CT image data altogether and to use the MR image data exclusively to generate volume images, including divergent volume images for localization, virtual simulation, and dosimetric RTP.

The present invention contemplates a new and improved method and apparatus which overcomes the above-referenced problems and others.

A primary object of the invention is to enable soft tissue tumor localization, virtual simulation, and dosimetric planning using magnetic resonance image data exclusively.

It is a further object of the invention to use magnetic resonance image data as the primary data set for soft tissue tumor localization, virtual simulation, and dosimetric planning.

It is another object of the invention to generate volume images from the acquired MR image data for soft tissue tumor localization, virtual simulation, and dosimetric planning.

A further object of the invention is to generate at least one divergent image of a volume of a patient from the acquired MR image data for soft tissue tumor localization, virtual simulation, and dosimetric planning.

Yet another object of the invention is to generate at least one of a digitally reconstructed "radiographic" image and a digitally composited "radiographic" image of a volume of a patient from the acquired MR image data for soft tissue tumor localization, virtual simulation, and dosimetric planning.

A still further object of the invention is to generate the volume images of the patient having selectable arbitrary thicknesses that can be changed substantially in real time.

These and other objects and advantages of the invention will become apparent to those skilled in the art upon a reading and understanding of the descriptions below.

SUMMARY OF THE INVENTION

In its preferred form, the invention provides a method of tissue localization and virtual simulation in a patient for radiation therapy planning. Using a magnetic resonance (MR) imaging device, the patient is scanned to generate a magnetic resonance image volume data set of the patient. Next, using the magnetic resonance image volume data set exclusively, an image of the patient is displayed on a human readable display device associated with the magnetic resonance imaging device based on the acquired magnetic resonance image volume data set. A target tissue is identified in the image of the patient displayed on the human readable display device. Lastly, at least one radiation therapy treatment boundary is defined in the image of the patient for radiation therapy treatment of the target tissue. Typically, up to twenty (20) multiple radiation therapy treatment boundaries are selected in the image so the healthy patient tissue between the tumor and the skin is not exposed to excessive radiation.

In another form of the invention, a method of tissue localization in virtual simulation in a patient is provided for radiation therapy planning. Using a magnetic resonance imaging device, the patient is scanned to generate a magnetic resonance image volume data set of the patient. Next, using the magnetic resonance image volume data set as the primary data set, an image of the patient is displayed on a human readable display device associated with the magnetic resonance imaging device based on the acquire magnetic resonance image volume data set. Other imaging modalities may be used to generate other image data to be used as secondary image data to aid in visualization. A target tissue is identified in the MR image of the patient displayed on the human readable display device. At least one radiation therapy treatment boundary is defined in the MR image of the patient for radiation therapy treatment of the target tissue.

In yet another form of the invention, a system is provided for tissue localization and virtual simulation in a patient for radiation therapy planning. The system includes a magnetic resonance imaging device for scanning a patient to generate a magnetic resonance image volume data set of the patient. A human readable display device associated with the magnetic resonance imaging device is used to display an image of the patient derived from the magnetic resonance image volume data set. A first processor is provided for use in identifying target tissue in the image of the patient displayed on the human readable display device. A second processor is provided for defining a radiation therapy treatment boundary in the image of the patient for radiation therapy treatment of the target tissue.

In accordance with the invention, the patient is scanned using the magnetic resonance imaging apparatus to produce a 3-D volume data set of the patient. The 3-D volume data set is transformed into a one of a multi-planar reformatted image (MPR), an oblique multi-planar reformatted image (OMPR), a digitally reconstructed "radiograph" (DRR), and a digitally composited "radiograph" (DCR).

In accordance with a more limited aspect of the invention, a location of the target tissue is defined relative to the patient. Further, the center of the target tissue is located. Still further, the radiation therapy treatment boundary is defined to include an optimal radiation treatment beam angle relative to the first area of the patient.

In accordance with yet a further limited aspect of the invention, a plurality of fiducial markers are placed on the patient before the step of performing the scan. After the optimal radiation treatment beam angle is defined, the patient is marked with a plurality of indicia relating the optimal radiation treatment beam angle and the location of the target tissue to the plurality of fiducial markers.

In a yet more further limited aspect of the invention, a volume of the target tissue is identified using the human readable display device. Further, an approximate centroid of the target tissue is calculated based on the identified volume of the target tissue.

Still further aspects and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments and are not be construed as limiting the invention.

DETAILED DESCRIPTION OF THE PREFERRED EMBODIMENTS

Figure 3:
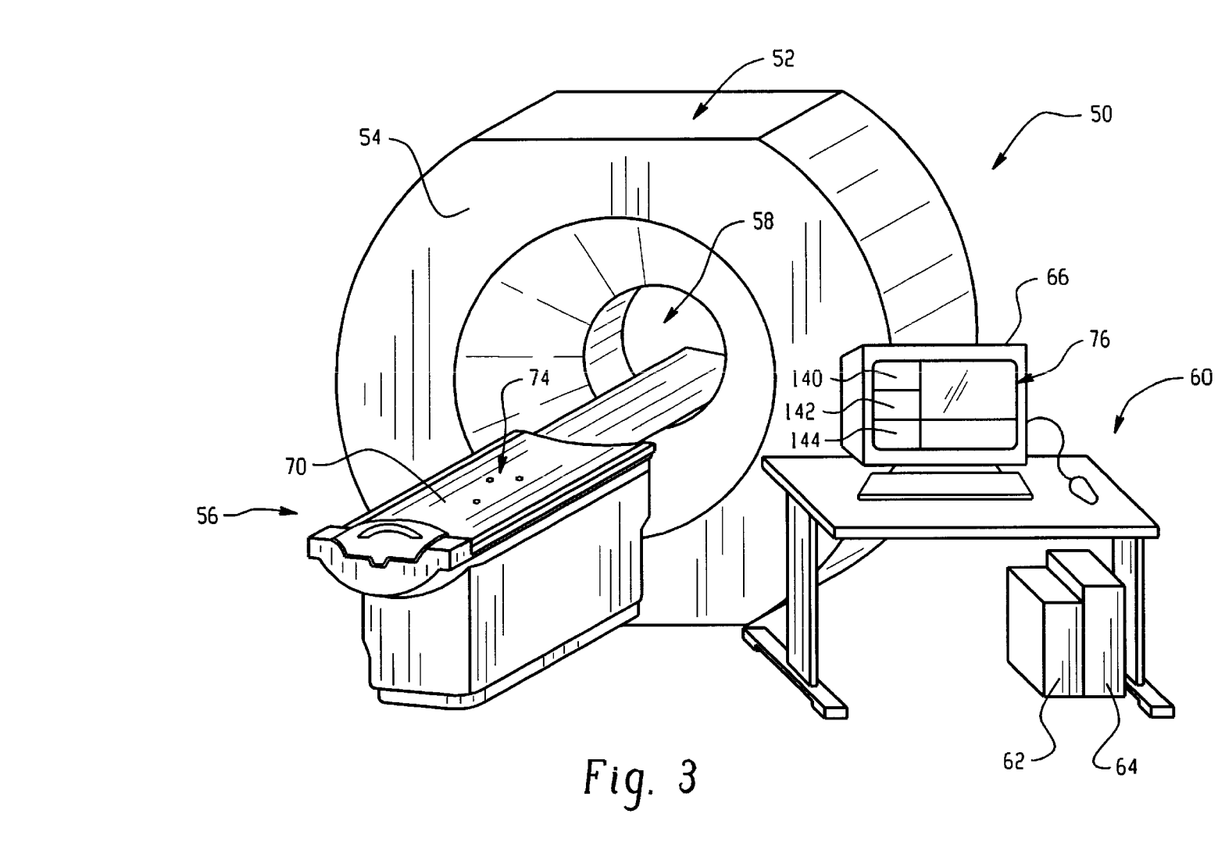
FIG. 3 is a diagrammatic illustration of a magnetic resonance imaging system for implementing the localization, virtual simulation, and dosimetric planning steps in accordance with the present invention.

Referring now to the drawings wherein the showings are for the purposes of illustrating the preferred embodiments of the invention only and not for purposes of limiting same, with reference first to FIG. 3, the subject system 50 includes a magnetic resonance (MR) imaging device 52 of the type well known in the art. As shown, the MR imaging device 52 includes a magnetic motive force means in the form of a magnet driver disposed in association with an annular ferromagnetic flux path 54. A retractable patient support 56 selectively supports a patient or subject to be examined in an air gap 58 defined by the annular ferromagnetic flux path 54. A control console 60 includes hardware and software processors 62, 64 provided with an energization and calibration system and suitable magnetic resonance electronics to set up a magnetic field across the air gap 58. Magnetic resonance of dipoles are induced in an imaging region and the resultant received magnetic resonance signals are processed by the software processors 62, 64 to create volume images on a human readable display device 66.

The patient support 56 includes a patient supporting surface 70 in a substantially horizontal plane. Preferably, the patient supporting surface is formed by a vinyl coated polyethylene foam core having a substantially trapezoidal cross section. The shape of the support together with the materials forming the support provide the desired rigidity suitable for MR imaging. Eight (8) pound EVA polyethylene foam material has been found to have the most desirable characteristics. The preferred construction of the supporting surface include the constraints that it is non-deformable, non-magnetic, capable of accepting lock bars for patient immobilization devices, non-distorting to the magnetic fields, and yields a zero (0) signal.

Overall, the supporting surface has a longitudinal axis lengthwise therealong and a perpendicular transverse axis thereacross, both in the horizontal plane. An elevation adjusting means (not shown) within a support frame 72 selectively adjusts the relative height of the supporting surface. The supporting surface is slidably mounted on the support frame 72 to provide a means for moving the supporting surface in the horizontal plane. Preferably, a suitable motor drive (not shown) is mounted to the frame 72 to drive the patient supporting surface therealong.

During a medical procedure using the subject system 50, the patient is positioned in the imaging apparatus 52. A plurality of fiducial markers 74 are placed on the patient. A three dimensional magnetic resonance volumetric image data set is then generated. The position of a plurality of fiducial markers 74 placed on the patient is stored in conjunction with the volumetric planning data such that the data is correlated with the patient image. The volumetric image data set is stored in a volumetric or planning data memory in the hardware and software processors 62, 64 at the control console 60. The operator control console 60 controls the volume planning image data memory or video processor such that selected volume images, parallel volume images, divergent volume images, projection images, surface renderings, and other conventional displays of the data are generated for display on a planning image display 76 of the human readable display device 66. Preferably, as will be described below, the planning image display 76 includes corresponding sagittal, coronal, and transverse axial slices through one or more selected common points of intersection.

Figure 4:
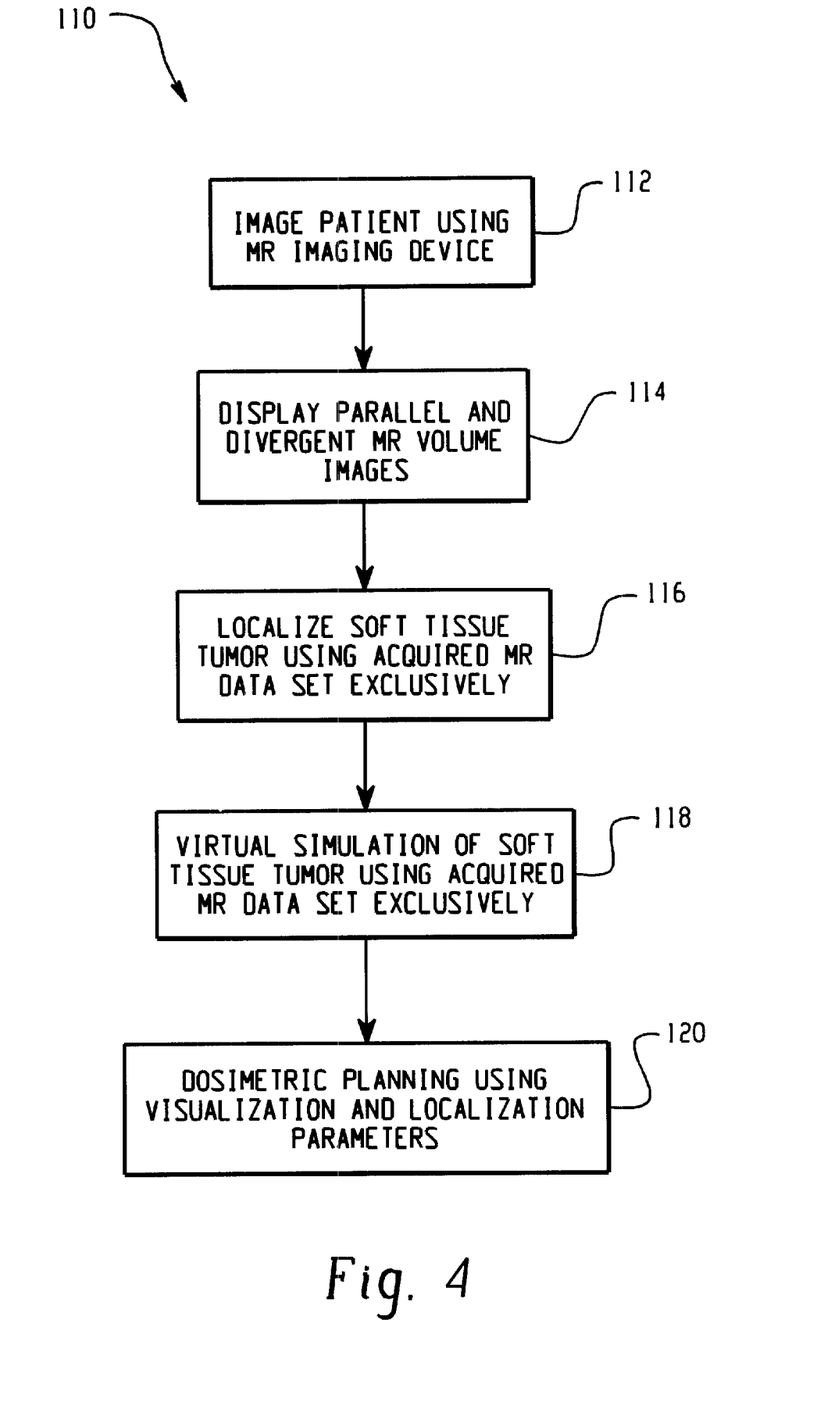
FIG. 4 is a flow chart illustrating the preferred method of localization, virtual simulation, and dosimetric radiation therapy planning for soft tissue tumors according to the present invention; and, FIG. 5 is an illustration showing an MR image on a display screen for soft tissue tumor localization, virtual simulation, and radiation therapy planning in accordance with the present invention.

With reference next to FIG. 4, the preferred method 110 in accordance with the present invention for localization, virtual simulation, and subsequent dosimetric planning is shown. Initially, in step 112, a patient is imaged with fiducial markers in the system 50 shown in FIG. 3 using the MR imaging device 52. An expected treatment volume is scanned using an optimized pulse sequence. The pulse sequence is tailored to provide for pathological visualization, and good bone marrow imaging. Additionally, the pulse sequence is optimized for artifact suppression and also for overall speed. At a minimun, the images are automatically corrected in the subject system for gradient distortion. As well, the images are automatically corrected for other types of distortion, if possible. Preferably, the three dimensional magnetic resonance image data set is acquired in less than ten (10) minutes.

Figure 5:
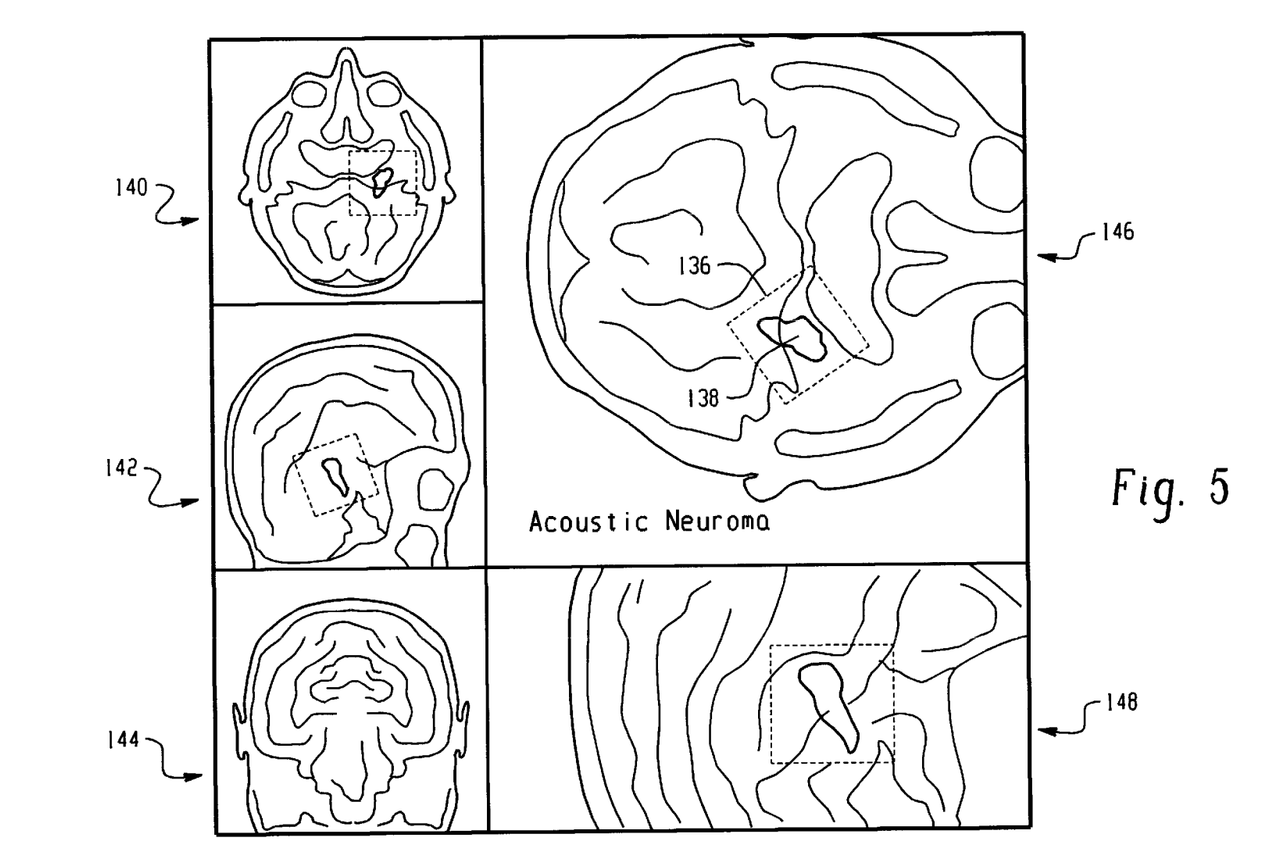

After the three dimensional magnetic resonance image data set is acquired, it is transferred to the radiation therapy planning workstation 60 whereat, in step 114, the image is displayed on the planning image display 66 for human observation. As noted above, the prior art technique attempted to use non-divergent 2-dimensional views of thin, but finite, images of fixed thickness processed off-line. This limitation, in conjuction with unacceptable distortion, led to abandonment of the technique. Preferably, therefore, in the subject system, the MR image is transformed into rendered volumes which are displayed in a manner as shown in FIG. 5. Further, the rendered volume images of the patient have an arbitrary thickness that is selectable substantially in real time. The displays appear to change substantially on-the-fly to a human observer.

With combined reference to FIGS. 4 and 5, the soft tissue tumor 138 is shown clearly in each of the views 140–148 of the patient as shown. The first three (3) views of the patient present volumetric parallel images derived from the acquired MR data set and aligned with the three (3) primary patient planes. More particularly, an axial multi-planar reformatted image 140, a sagittal multi-planar reformatted image 142, and a coronal multi-planar reformatted image 144 are displayed as shown in FIG. 5. In addition, a divergent image 146 is shown in the upper right hand corner of the display device. The divergent image is a digitally composited and/or reconstructed "radiographic" image 146. Lastly, an oblique multi-planar reformatted image 148 is presented on the lower right hand corner of the display 76 substantially as shown.

A soft tissue tumor is localized in step 116 using the acquired MR image data set exclusively. A treatment isocenter is localized using at least one of the following methods: bi-planar DRR fluoroscopy, bi-planar DCR fluoroscopy, and tumor centroid calculation using post contouring calculation. A target boundary 136 is drawn around the soft tissue tumor 138 to complete the localization.

The step of displaying the images includes rendering volume images of the patient having an arbitrary thicknesses that are selectable substantially in real time. The display method preferably includes rendering the volume images of the patient with thicknesses that are modifiable in no more than two (2) or three (3) seconds. This image update rate is considered in the art to be substantially "real time" and looks to be on-the-fly to a human observer.

Next, in step 118, virtual simulation is executed on the soft tissue tumor image using the acquired MR image data set exclusively. More particularly, the acquired MR image data set is used as the primary data set. The virtual simulation includes defining treatment boundaries and beam modifiers on the DRR, DCR, MPR, or OMPR images. In the virtual simulation step 118, the optimal radiation treatment beam angles to the soft tissue tumor 138 are calculated. Additionally, beam modifiers are placed so that certain areas within the patient are blocked out to prevent them from being irradiated during the subsequent radiation therapy.

Lastly, in step 120, dosimetric planning is executed using the visualization and localization parameters derived in the localization 116 and virtual simulation 118 steps.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A method of tissue localization and virtual simulation in a patient for radiation therapy planning, the method comprising the steps of:
    using a magnetic resonance imaging device, scanning the patient to develop a magnetic resonance image volume data set of the patient;
    correcting said magnetic resonance image volume data set for distortion to generate a distortion corrected magnetic resonance image volume data set; and,
    using said distortion corrected magnetic resonance image volume data set exclusively:
        displaying an image of the patient on a human readable display device associated with the magnetic resonance imaging device based on said magnetic resonance image volume data set;
        identifying a target tissue in the image of the patient displayed on said human readable display device; and,
        defining at least one radiation therapy treatment boundary in the image of the patient for radiation therapy treatment of said target tissue.

2. The method according to claim 1 wherein the step of displaying includes rendering a volume image of the patient on the human readable display.

3. The method according to claim 2 wherein the step of rendering includes rendering a volume image of the patient having a selectable arbitrary thickness.

4. The method according to claim 2 wherein the step of rendering said volume image of the patient includes generating at least a one of a digitally reconstructed image and a digitally composited image of the patient based on said magnetic resonance image volume data set.

5. The method according to claim 4 wherein:
    the step of identifying said target tissue includes defining a location of the target tissue in the image of the patient and locating an isocenter of the target tissue; and,
    the step of defining said at least one radiation therapy treatment boundary includes defining an optimal radiation treatment beam angle relative to said image of the patient.

6. The method according to claim 5 further including the steps of:
    placing a plurality of fiducial markers on the patient before said step of scanning the patient; and,
    after defining said optimal radiation treatment beam angle, marking the patient with a plurality of indicia relating said optimal radiation treatment beam angle and said location of said target tissue to said plurality of fiducial markers.

7. The method according to claim 6 further including the steps of:
    using said human readable display device and said operator interface device, identifying a volume of said target tissue; and,
    calculating an approximate centroid of the target tissue based on said identified volume of the target tissue.

8. The method according to claim 1 wherein:
    the step of scanning includes scanning the patient to develop a 3-dimensional image volume data set of said patient; and,
    the step of displaying includes generating a divergent image of the patient based on said 3-dimensional image volume data set and displaying the divergent image on said human readable display device.

9. The method according to claim 8 wherein the step of displaying the divergent image includes displaying at least a one of a digitally reconstructed image of the patient and a digitally composited image of the patient on said human readable display device.

10. The method according to claim 9 wherein:
    the step of identifying said target tissue includes defining a location of the target tissue in the image of the patient and locating an isocenter of the target tissue; and,
    the step of defining said at least one radiation therapy treatment boundary includes defining an optimal radiation treatment beam angle relative to said image of the patient.

11. The method according to claim 10 further including the steps of:
    placing a plurality of fiducial markers on the patient before said step of scanning the patient; and,
    after defining said optimal radiation treatment beam angle, marking the patient with a plurality of indicia relating said optimal radiation treatment beam angle and said location of said target tissue to said plurality of fiducial markers.

12. The method according to claim 11 further including the steps of:
    using said human readable display device and said operator interface device, identifying a volume of said target tissue; and,
    calculating an approximate centroid of the target tissue based on said identified volume of the target tissue.

13. The method according to claim 1 wherein:
    the step of scanning includes scanning the patient to develop a 3-dimensional image volume data set of said patient; and,
    the step of displaying includes generating a parallel image of the patient based on said 3-dimensional image volume data set and displaying the parallel image on said human readable display device.

14. The method according to claim 13 wherein the step of displaying the parallel image includes displaying at least one of a multi-planar reformatted image of the patient and an oblique multi-planar reformatted image of the patient.

15. The method according to claim 1 wherein the step of display includes rendering a volume image of the patient having an arbitrary thickness that is selectable substantially in real time.

16. The method according to claim 15 wherein the step of rendering the volume image includes rendering the volume image of the patient with a thickness that is modifiable substantially in real time to a human observer.

17. The method according to claim 1, wherein the step of correcting said image volume data set includes correcting said image volume data set for gradient distortion.

18. The method according to claim 17, further including the step of correcting said image volume data set for distortion other than gradient distortion.

19. A system for tissue localization and virtual simulation in a patient for radiation therapy planning, the system comprising:
- a magnetic resonance imaging device for scanning the patient to develop a magnetic resonance image volume data set of the patient;
- means for correcting said magnetic resonance image volume data set for distortion to form a distortion corrected magnetic resonance image volume data set;
- a human readable display device associated with the magnetic resonance imaging device for displaying an image of the patient based on said distortion corrected magnetic resonance image volume data set exclusively;
- first processing means for identifying a target tissue in the image of the patient displayed on said human readable display device; and,
- second processing means for defining at least one radiation therapy treatment boundary in the image of the patient for radiation therapy treatment of said target tissue.

20. The system according to claim 19 wherein the human readable display device includes means for rendering a volume image of the patient.

21. The system according to claim 20 wherein the means for rendering includes means for rendering a volume image of the patient having a selectable arbitrary thickness.

22. The system according to claim 19 wherein:
- the magnetic resonance imaging device is adapted to scan the patient to develop a 3-dimensional image volume data set of the patient; and,
- the human readable display device includes means for generating a divergent image of the patient based on said 3-dimensional image volume data set and displaying the divergent image.

23. The system according to claim 22 wherein the human readable display device includes means for displaying the divergent image as at least a one of a digitally reconstructed image of the patient and a digitally composited image of the patient.

24. The system according to claim 19 wherein:
- the magnetic resonance imaging device is adapted to scan the patient to develop a 3-dimensional image volume data set of the patient; and,
- the human readable display device includes means for generating a parallel image of the patient based on said 3-dimensional image volume data set and displaying the parallel image.

25. The system according to claim 24 wherein the means for displaying includes means for displaying the parallel image as at least a one of a multi-planar reformatted image of the patient and an oblique multi-planar reformatted image of the patient.

26. The system according to claim 19 wherein the display device includes means for rendering a volume image of the patient having an arbitrary thickness that is selectable substantially in real time.

27. The system according to claim 26 further including means for rendering the volume image of the patient with a thickness that is modifiable substantially in real time to a human observer.

28. The system according to claim 19, wherein said means for correcting is adapted to correct said magnetic resonance image volume data set for gradient distortion.

29. The system according to claim 28, wherein said means for correcting is adapted to correct said magnetic resonance image volume data set for distortion other than gradient distortion.

30. A method of tissue localization and virtual simulation in a patient for radiation therapy planning, the method comprising the steps of:
- scanning the patient to develop a magnetic resonance image volume data set of the patient;
- correcting said magnetic resonance image volume data set for distortion; and,
- using said distortion corrected magnetic resonance image volume data set as a primary data set:
  - displaying an image of the patient based on said primary data set;
  - identifying a target tissue in the image of the patient; and,
  - defining at least one radiation therapy treatment boundary in the image of the patient for radiation therapy treatment of said target tissue.

31. The method according to claim 30 wherein the step of displaying includes rendering a volume image of the patient.

32. The method according to claim 30 wherein:
- the step of scanning includes scanning the patient to develop a 3-dimensional image volume data set of said patient; and,
- the step of displaying includes generating a divergent image of the patient based on said 3-dimensional image volume data set and displaying the divergent image of the patient.

33. The method according to claim 30 wherein:
- the step of scanning includes scanning the patient to develop a 3-dimensional image volume data set of said patient; and,
- the step of displaying includes generating a parallel image of the patient based on said 3-dimensional image volume data set and displaying the parallel image of the patient.

34. The method according to claim 30 wherein the step of displaying includes rendering a volume image of the patient having an arbitrary thickness that is selectable substantially in real time.

35. The method according to claim 30, wherein the step of correcting said image volume data set includes correcting the image volume data set for gradient distortion.

36. The method according to claim 35, further including the step of automatically correcting said image volume data set for distortion other than gradient distortion.

* * * * *